(12) United States Patent
Xu et al.

(10) Patent No.: US 7,037,904 B2
(45) Date of Patent: May 2, 2006

(54) USE OF N-ACETYL-D-GLUCOSAMINE IN THE MANUFACTURE OF PHARMACEUTICAL USEFUL FOR SUPPRESSING SIDE-EFFECT OF RADIOTHERAPY AND CHEMOTHERAPY

(75) Inventors: Qiwang Xu, Chongqing (CN); Junkang Liu, Chongqing (CN); Zetao Yuan, Chongqing (CN)

(73) Assignees: Third Military Medical University, Chinese People's Liberation Army, P.R. of China, Chongqing (CN); Bio-Wave Institute of Suzhou Hi-Tech New District Corporation, LTD, Jiangsu (CN); Beijing Sino-Hongkong Dafu Science & Technology of Biowave Co., Ltd., Beijing (CN)

( * ) Notice: Subject to any disclaimer, the term of this patent is extended or adjusted under 35 U.S.C. 154(b) by 0 days.

(21) Appl. No.: 10/469,327

(22) PCT Filed: Feb. 28, 2002

(86) PCT No.: PCT/CN02/00119

§ 371 (c)(1),
(2), (4) Date: Dec. 17, 2003

(87) PCT Pub. No.: WO02/067946

PCT Pub. Date: Sep. 6, 2002

(65) Prior Publication Data

US 2004/0077596 A1    Apr. 22, 2004

(30) Foreign Application Priority Data

Feb. 28, 2001   (CN) .............................. 01104882 A

(51) Int. Cl.
*A01N 43/04* (2006.01)
*A61K 31/70* (2006.01)
(52) U.S. Cl. .......................................... 514/62; 514/23
(58) Field of Classification Search .................. 514/62; 536/55.2
See application file for complete search history.

(56) References Cited

U.S. PATENT DOCUMENTS 4,216,208 A * 8/1980 De Barbieri .................... 514/8
4,710,493 A * 12/1987 Landsberger ................. 514/56
5,811,410 A * 9/1998 Falk et al. ..................... 514/54

FOREIGN PATENT DOCUMENTS

| CN | 1156026 | 8/1997 |
| CN | 1156027 | 8/1997 |
| CN | 1156028 | 8/1997 |
| WO | 93/14765 | 8/1993 |
| WO | 93/18775 | 9/1993 |

* cited by examiner

*Primary Examiner*—James O. Wilson
*Assistant Examiner*—Traviss C. McIntosh, III
(74) *Attorney, Agent, or Firm*—Ladas & Parry LLP

(57) ABSTRACT

The present invention has disclosed a use of N-acetyl-D-glucosamine in the manufacture of a medicament for inhibiting the side effect of radio-chemical therapy, the medicament with N-acetyl-D-glucosamine as main active component can be used to inhibit the side effect of radio-chemical therapy of cancer patients, with an effective rate up to 85%.

16 Claims, No Drawings

USE OF N-ACETYL-D-GLUCOSAMINE IN THE MANUFACTURE OF PHARMACEUTICAL USEFUL FOR SUPPRESSING SIDE-EFFECT OF RADIOTHERAPY AND CHEMOTHERAPY

TECHNICAL FIELD

The present invention relates to the use of N-acetyl-D-glucosamine and pharmaceutical acceptable salts thereof in the manufacture of a medicament for inhibiting the side effect of radio-chemical therapy.

BACKGROUND ART

After accepting radio-chemical treatment, patients with neoplasm often have marrow inhibition, hemogram variation, anemia, leucocyte reduction, protein synthesis inhibition and other reflections in dysfunction of metabolism, and they will be quickly accompanied with systematical side effects of radio-chemical therapy: nausea, vomiting, lack energy, appetite decreasing, loss of the hair and so on, the severer may have acute exhaustion or respiratory distress; as leucocytes decreasing may lead to immune dysfunction, systematical infection is likely to happen; furthermore, with the disturbance of the production of immune cells, most of the patients with neoplasm are finally dead from the whole body exhaustion, cachexia, infection and so on, these are almost resulted from the side effect of radio-chemical therapy. Therefore the control of side effect of radio-chemical therapy is contributed to the long period therapy of neoplasm and to strengthen the support ability of neoplasm patient to the therapy; at the same time, lighten the patient's pain in the course of treatment, and avoid a serious of complication caused by neoplasm. At present, supporting therapies commonly used clinically are mainly symptomatic treatments: for instance, when the patient lacks energy□ administration of energy mixture is adopted; when water electrolyte is disordered, supplying water electrolyte is adopted; when vomiting is serious, anti-vomiting medicine is administrated; when the patient is infected, anti-inflammation therapy is used, and so on. The effects of these symptomatic treatments do not have good effect. The side effect after radio-chemical therapy almost happens to the each patient with neoplasm who has been treated, making them suffered from pain, and this is a big problem in the neoplasm treatment. Therefore, a medicament capable of inhibiting the side effect caused by radio-chemical therapy is quite needed in the field of neoplasm treatment.

In the research of "bio-waves" theory, the present inventor has set up a bacterial wave growth model. Through researching, it is known that this wave is of its intrinsic regulation mechanism: some chemical substances are able to participate the regulation in the bio-wave process, so as to transform an abnormal periodic slow wave into a normal physiological chaotic quick wave, and this kind of substances are known as promoting wave factors. Through separating, purifying and identifying, it is determined that one of the factors is N-acetyl-D-glucosamine, the promoting wave function of which is shown in lubricating and protecting the cell. Many biochemical and physiological process of human body need the participation of the promoting wave factors, and it would lead to an abnormal state, if this kind of promoting wave factors is lacked in the living body.

N-acetyl-D-glucosamine is a chemical reagent. From the 1990's, it is continually used to treat pericementitis (WO9102530A1), microbiological infection (WO9718790A3), intestinal inflammation (WO9953929A1), cornea disease (JP10287570A2), hypertrophy of the prostate (US05,116,615) and so on. It is also applied in cosmetology (JP59013708A2), shampoo preparation (JP2011505A2), tissue growth regulation agent (WO/A 8 702244), and etc., but it has not been used in the manufacture of a medicament for inhibiting the side effect of radio-chemical therapy.

CONTENTS OF THE INVENTION

The applicant of the present invention finds that N-acetyl-D-glucosamine and pharmaceutical acceptable salt thereof are able to effectively inhibit the occurrence and serious degree of the side effect of radio-chemical therapy.

Therefore, the present invention is related to the use of N-acetyl-D-glucosamine and pharmaceutical acceptable salt thereof in the manufacture of a medicament for inhibiting the side effect of radio-chemical therapy.

On the other hand, the present invention is related to a method for inhibiting the side effect of radio-chemical therapy, including administrating to a patient who is in need thereof an effective amount of N-acetyl-D-glucosamine or pharmaceutical acceptable salts thereof.

The structure of N-acetyl-D-glucosamine is as follows:

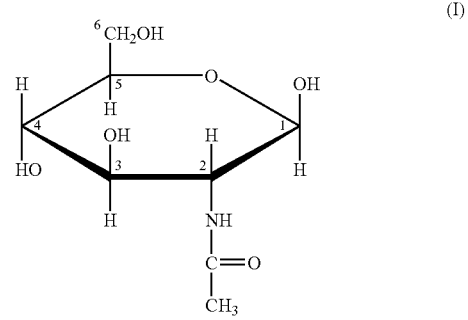

N-acetyl-D-glucosamine can be purchased in the market or prepared according to known methods. For instance, patent application WO97/31121 has disclosed a method for preparing N-acetyl-D-glucosamine from chitin by enzyme method, Japanese patent application JP63273493 has disclosed a method in which chitin is partially hydrolyzed into N-acetyl-chitose, and then it is treated with enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids, such as hydrochloride, hydrobromide, borate, phosphate, sulfate sulfite and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate, α-glyceryl phosphate and glucose-1-phosphate.

The compound of formula (I) or pharmaceutical acceptable salts thereof can be used as active agent to be combined with many kinds of pharmaceutical acceptable excipients or/and carriers, by the way of mixing, granulation, tableting, sugar coating or film coating and so on, it can be formulated into liquid or solid preparations, so as to be used to inhibit the side effect of radio-chemical therapy The compound of formula (I) or pharmaceutical acceptable salts thereof can be administrated parenterally, for instance, by intravein injection, intramuscle injection, or orally. The dosage dependents on the age, body weight, disease condition of the patient, the administration manner and the specific method of radio-chemical to treat the neoplasm. The compound of formula (I) or pharmaceutical acceptable salts thereof can be administrated several days (for instance 3~10 days) before performing the radio-chemical therapy for anti-neoplasm, then administrate the medicament in combination with radio-chemical therapy for anti-neoplasm; or directly administrate the medicament with the combination of radio-chemical therapy for anti-neoplasm; it is also effective to administrate the said medicament after the radio-chemical therapy for anti-neoplasm is started and the side effect has been emerged. A suitable dosage for the adult to be administrated is about 200~10000 mg/day, intravein injection preferably is once daily, oral or intramuscle injection preferably is three times daily. It is suggested that seven days is a course of treatment, and continue the administration for 2~3 courses of treatment.

Conventional methods can be used to formulate the phmarceutical compositions in the form of suitable pharmaceutical preparations, for instance, the preparations in the form of liquid for intravein injection or oral administration may use aseptic water or aseptic saline solution as carriers. The suspensions or solutions for intramuscle injection may use aseptic water, olive oil, ethyl oleate, diols and other medically acceptable carriers. In the form of solid formulation for oral administration, such as tablet or capsule, beside of the compound of formula (I), it may also include diluent, such as lactose, glucose, cellulose, starch, lubricant such as silica, talc, magnesium stearate or calcium stearate, and/or polyglycol; binder such as starch, Arabic gum, methyl cellulose, carboxymethyl cellulose, polyvinylpyrrolidone; depolymerizing agent such as starch, alginic acid, aliginate, starch sodium glycolate; foaming mixture; colorant; sweetener; lubricant such as lecithin, polyethenoxy ether and so on. Said preparations can be prepared by the known processes, such as mixing, granulation, tableting, sugar coating or film coating and so on.

Though having no intention to be limited by any theories, the present inventor thinks that, the continuous wave of normal organism executes the physiological function by the way of rhythmical life activity of tissue cell. This wave process is a chaos process, by which the adaptation to the outside world can be maintained. Chaos wave process of the organism dependents upon the systematical synergism and unification of various tissues. In the process of treating neoplasm by radio-chemical therapy, not only the enzyme is subjected to influence synthetically, but the function of existing enzyme protein also have obstacles, furthermore, the metabolic activity is affected, to make the systematical coupling oscillation dispersed, incapable of emerging great function activity, and showing a non-rhythmical process of life activity, that is, a successive reaction, leading to various side effects. Thus, the control of radio-chemical therapeutic side effect would be focused on protecting the function of existing protein. N-acetyl-D-glucosamine possesses a characteristic of promoting bio-waves, and it is believed that, through regulating the oscillation of enzyme protein, the systematical function of the organism and the process of recovering rhythm of organism can be regulated. On one hand, it exerts the systematical effect to organism for resisting the stimulation of unfavorable factors, adapts to the outside world; on the other hand, it regulates the oscillation of enzyme protein, remove unfavorable influence of the environment, moreover, relieve or control the side effect of radio-chemical therapies.

OPTIMAL MODE FOR CARRYING OUT THE INVENTION

The following experimental examples are used to illustrate the promoting wave function, low toxicity, and the effect for inhibiting the side effect of radio-chemical therapy, of the compound of the present invention (the compound of formula (I)).

I. Promoting Wave Test of the Compound of Formula (I)
  1. Experimental Materials and Method:
  1.1 Samples: Pure Compound of Formula (I)
  1.2 Experimental Materials:
  Strain: Proteus Mirabilis (which should comply with the following biological reaction characteristics: dynamics (+), urease (+), lactose (−), glucose (+), $H_2S$ (−), phenylalanine deaminase (+).
  Culture medium: modified LB culture medium (the components of the composition are: trytones of 1%, yeast extract of 0.5%, sodium chloride 1%, glucose of 0.1%, TTC of 0.002% and pH=7.2~7.4).
  1.3 Experimental Method:
  The Proteus Mirabilis were inoculated at the center of LB plate, incubating at 37° C. for 9 hours, then there were concentric rings emerged, which were extended outward continually with an interval of 3 hours, and this was taken as a control; adding the compound of formula (I) with final concentration of 0.5% onto the LB plate, The Proteus Mirabilis were innoculated by the same method, cultured at 37° C., and the result showed that not only the concentric rings formed with an interval of 3 hours were emerged, comparing with the control, it can be seen that there were also many fine waves on each ring emerged.
  2. Experimental Results and Evaluation:
  The experiment adopts a bio-wave model which is used to research the promoting wave function of the compound of formula (I). It can be seen from the result that the compound of formula (I) was not only able to cause bacterial cell to reveal a normal bio-wave characteristic, but also cause the wave reveal finer wave mode, and these indicated that the compound of formula (I) have promoting function to bio-waves, and the promoting wave function is able to participate the reparation and re-distribution function of the cells of skin.

II. Toxicological Test of the Compound of Formula (I), Including:
1. acute toxicity test: including tests of administrating medicine by oral, Intravenous injection and maximum limit amount for administration;
2. Ames test;
3. micronucleus test of bone marrow cell of mouse;
4. abnormal sexual test for the sperm of mouse;
5. abnormal aberrance test for the chromosin of mouse's testis;
6. chronic lethal test;
7. subchronic toxicity (feed for 90 days) test;
8. traditional aberrance-inducing test;
  The results from these tests show that in the acute toxicity test of the compound of formula (I), the dosage more than 2 g/kg is taken, which is 300 times than the injection dosage for human being, but the acute toxicosis reaction had not appeared yet; in the long-period toxicity test, the maximum dosage has reached up to 1 g/kg, and after the treatment and observation for four weeks, there is no toxicosis reaction yet; and in the reproduction test, the mouse was fed with routine dosages from 7 mg/kg for 3 generations, it has been proved that the compound of formula (I) has no influence on the pregnancy, birth, nurse and the growth of baby mice, so it is proved that the compound of formula (I) is a substance without toxicity.

III. Observation of Curative Efficiency.

It is known from observation of the clinic trial that the bio-wave capsule (containing 600 mg of N-acetyl-D-glucosamine in each granule) of the present application has an excellent effect to control the side effect in the process of radio-chemical therapy for treating the patient suffered from the leukaemia, Hodgkin's disease and the neoplasm of liver, stomach and so on, with a total effective rate of 85%, a part of typical cases are as follows:

1. Mr. Zhang, male, suffered from leukaemia, after radio-chemical treatment, appeared uncomfortable phenomenons of weak, lacking energy all over the body, appetite decreasing, often vomiting and so on, so the condition of his body was very worse. A week after administrating the bio-wave capsule of the invention, his can eat as the normal, meanwhile the dreaminess, palpitation and other bad sleeping situations were relieved. After that, continuously administrate the medicine, his lack of energy was recovered while and the number of catching cold was remarkably decreased.

2. Ms. Chen, come from Nanchong, Sichuan province, female, suffered from stomach cancer, after radio-chemical treatment, her body become thin, the immunity condition was reduced, companied with appetite diminishing and bad emotion. Administrating the bio-wave capsule of the invention 3 times a day, 1~2 capsules each time, after a week, her feeling gradually became better, and some bad symptoms was improved without any side effect, continuously administrate the medicine.

The invention claimed is:

1. A method for treating a cancer patient who is undergoing or has undergone a radiation therapy or chemotherapy treatment, the method comprising administering to said patient a medicament comprising N-acetyl-D-glucosamine of the following formula (I) or a pharmaceutically acceptable salt thereof:

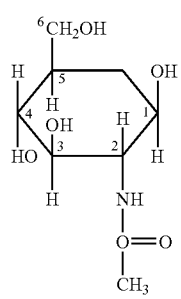

said medicament being administered to the patient in an amount effective to reduce the incidence or severity of at least one side effect of said radiation therapy or chemotherapy treatment.

2. The method according to claim 1, wherein the at least one side effect is selected from the group consisting of nausea, vomiting, decreased energy, diminished appetite, cachexia and immune dysfunction.

3. The method according to claim 2, wherein the medicament is administered to the patient after said radiation therapy or chemotherapy treatment.

4. The method according to claim 2, wherein the medicament is administered to the patient with said radiation therapy or chemotherapy treatment.

5. The method according to claim 2, wherein the medicament is administered to the patient before and with said radiation therapy or chemotherapy treatment.

6. The method according to claim 1, wherein the at least one side effect is selected from the group consisting of lack of energy, sleeplessness, palpitation, diminished appetite and feelings of weakness.

7. The method according to claim 6, wherein the medicament is administered to the patient after said radiation therapy or chemotherapy treatment.

8. The method according to claim 6, wherein the medicament is administered to the patient with said radiation therapy or chemotherapy treatment.

9. The method according to claim 6, wherein the medicament is administered to the patient before and with said radiation therapy or chemotherapy treatment.

10. The method according to claim 1, wherein the medicament is administered to the patient orally, intravenously or intramuscularly.

11. The method according to claim 1, wherein the patient is an adult patient and the medicament is administered to the adult patient at a dosage of 200–1000 mg N-acetyl-D-glucosamine.

12. The method according to claim 10, wherein the patient is an adult patient and the medicament is administered to the adult patient at a dosage of 200–1000 mg N-acetyl-D-glucosamine.

13. The method according to claim 1, wherein the medicament consists essentially of N-acetyl-D-glucosamine of formula I or a pharmaceutically acceptable salt thereof.

14. The method according to claim 1, wherein the medicament consists of N-acetyl-D-glucosamine of formula I or a pharmaceutically acceptable salt thereof.

15. The method according to claim 1, wherein the medicament consists essentially of N-acetyl-D-glucosamine of formula I.

16. The method according to claim 1, wherein the medicament consists of N-acetyl-D-glucosamine of formula I.

* * * * *